(12) United States Patent
Akman et al.

(10) Patent No.: US 10,213,489 B2
(45) Date of Patent: Feb. 26, 2019

(54) THREE DIMENSIONAL HEALING KIT

(71) Applicants: Serhan Akman, Konya (TR); Mustafa Tunali, Yenimahalle/Ankara (TR)

(72) Inventors: Serhan Akman, Konya (TR); Mustafa Tunali, Yenimahalle/Ankara (TR)

( * ) Notice: Subject to any disclaimer, the term of this patent is extended or adjusted under 35 U.S.C. 154(b) by 0 days.

(21) Appl. No.: 15/555,713

(22) PCT Filed: Mar. 3, 2016

(86) PCT No.: PCT/TR2016/050053
§ 371 (c)(1),
(2) Date: Sep. 5, 2017

(87) PCT Pub. No.: WO2016/140638
PCT Pub. Date: Sep. 9, 2016

(65) Prior Publication Data
US 2018/0055912 A1 Mar. 1, 2018

(30) Foreign Application Priority Data
Mar. 5, 2015 (TR) .................................. 2015/02615

(51) Int. Cl.
*A61C 8/02* (2006.01)
*C12N 5/00* (2006.01)
*A61K 33/24* (2006.01)
*A61K 33/42* (2006.01)
*A61K 38/36* (2006.01)
*A61L 24/10* (2006.01)

(52) U.S. Cl.
CPC .......... *A61K 38/363* (2013.01); *A61C 8/0006* (2013.01); *A61K 33/24* (2013.01); *A61K 33/42* (2013.01); *A61K 38/366* (2013.01); *A61L 24/106* (2013.01); *A61L 2400/04* (2013.01); *C12N 5/0062* (2013.01)

(58) Field of Classification Search
CPC ... A61K 9/0024; A61K 38/363; A61L 27/225; A61L 27/56; A61L 2400/04; A61L 24/106; C07K 14/75; C12N 2533/56; C12N 5/0062
See application file for complete search history.

(56) References Cited

FOREIGN PATENT DOCUMENTS

| JP | 2001242164 A | * | 9/2001 | |
|---|---|---|---|---|
| JP | 2001242164 A | | 9/2001 | |
| KR | 101008583 B1 | | 1/2001 | |
| KR | 101008583 B1 | * | 1/2011 | |
| WO | 2004/050102 A2 | | 6/2004 | |
| WO | WO-2004050102 A2 | * | 6/2004 | ........... A61L 24/106 |

OTHER PUBLICATIONS

JP-2001242164-A, Espacenet English Translation of application, downloaded Jun. 2018 (Year: 2018).*
KR-101008583-B1, Espacenet English Translation of application, downloaded Jun. 2018 (Year: 2018).*
International Search Report of PCT/TR2016/050053, dated Jun. 22, 2016.
Tlbgroup:"PFR Plugus", Nov. 3, 2011 (Nov. 3, 2011), p. 1, XP054976585, Retrieved from the Internet: URL:https://www.youtube.com/watch?v=NfDIOV.

* cited by examiner

*Primary Examiner* — Mark V Stevens
(74) *Attorney, Agent, or Firm* — Gokalp Bayramoglu

(57) ABSTRACT

Invention; is about the kit that enables three-dimensional healing with the platelet-rich fibrin framework support used in hard and soft tissue healing.

8 Claims, 5 Drawing Sheets

THREE DIMENSIONAL HEALING KIT

TECHNICAL FIELD

Figure 1:
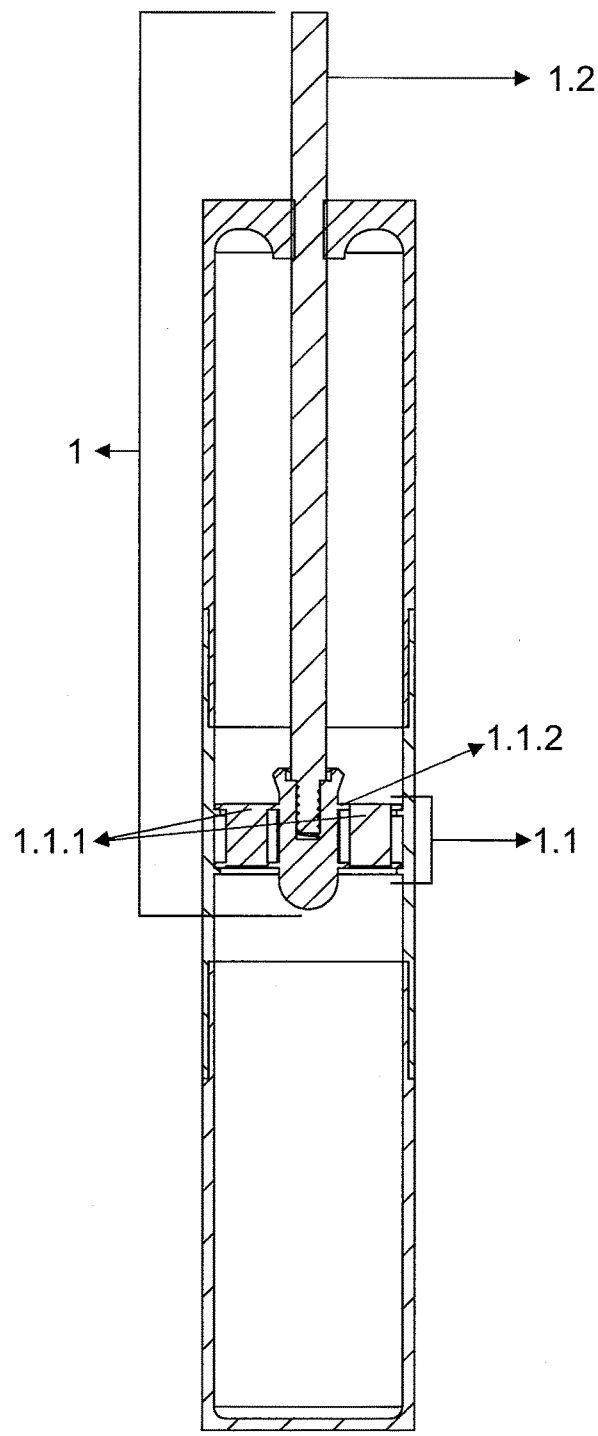

Invention; is about the kit that enables three-dimensional healing with the platelet-rich fibrin framework support used in hard and soft tissue healing.

PREVIOUS TECHNIC

Blood clotting (Coagulation): Clotting is very vital for body as it prevents blood from releasing the vessel in case of blood vessel injuries. The substance in circulation called fibrinogen is transformed into insoluble fibrin that is the frame of the clotting. Until now, 13 factors have been found effective in clot formation. If they all function regularly, the factor called prothrombin in circulation is changed into thrombin by the substance that released from the damaged tissue and this is effective in transforming the fibrinogen into fibrin. Calcium in the blood and blood cells called platelets have a great role in this event. Platelets are bone marrow-derived cells. These cells gather in the injury area when the blood vessel wall is cut or torn and form a trombus that prevents small leakage. This is called "primary hemostatic trombus". This trombus will temporarily stop the bleeding. Later, the second phase of coagulation, that is, "hemostasis" with the substances released from both the platelets and the vessel wall take place. As soon as the coagulation starts as a result of an injury of a blood vessel, clot soon will start, the plasmin that occurs in the same wound takes control of the clot and within a day, as many reactions in the body occurs.

Three mechanisms that occur in order are effective in clotting.

1. The formation of a complex called prothrombin activator as a result of chemical reaction developed in respond to vessel rupture or damage to the blood itself.
2. Conversion of prothrombin to thrombin under the influence of prothrombin activator.
3. Thrombin's turning the fibrinogen to fibrin strands, and strands of fibrin's forming clot involving platelets, blood cells and plasma.

The fibrin strands formed as a result of these three mechanisms occured in order adhere each other comprising blood cells and other substances. The resulting mass is called clot.

Prothrombin which is a precursor of thrombin is a plasma protein. Prothrombin is a plasma protein with α-2 globulin structure. It is synthesized in the liver. It can easily be broken into small pieces. One of them is thrombin. Vitamin K is required for its synthesis.

The effect of thrombin in fibrin formation:
The formation of blood clots
Clot retraction (shrinkage)—Serum
Vicious cycle of clot formation Together with the release of clotting factors and the conversion of fibrinogen to fibrin, this patch formed with platelets is strengthened and reinforced. Finally, the excess formed in this patch on the vessel wall is removed and the vessel is repaired.

In addition to coagulation, platelets undertake various tasks in soft tissue and bone healing, repair and maturation of body tissues. These cells also contain a number of cytokines and growth factors.

Of the key growth factors, platelet derived growth factor AB (PDGF-AB), transforming growth factor β-1 (TGFβ-1), vascular endothelial growth factors (VEGF) are predominantly concentrated in platelets. These growth factors have the potential to stimulate cell proliferation, tissue matrix remodeling and angiogenesis. Furthermore, the fibrinogen is found in high amounts in platelet α-granules and plays a decisive role in platelet aggregation during hemostasis. Fibrinogen is the end product of all coagulation reaction. Fibrinogen, a soluble protein, is converted to an insoluble fibrin structure through thrombin. Polymerized fibrin gel forms the first cicatricial matrix of the injured area. Having evolved into a biological glue, this structure creates a protective wall to the vascular structure around the platelet first aggregated during coagulation.

After a better understanding of the role of platelets in the wound healing, it has been proposed to use these cells in therapy.

Using the blood-derived products in stimulation of wound healing and wound closure started 40 years ago.

Platelet Rich Plasma (PRP): PRP technique is basically made with two centrifugal methods. Through adding clotting inhibitors into the tube during the first centrifugation, blood is separated into its layers without being clotted. Then, PRP product is obtained from the portion of platelet-rich blood in the second centrifugation made with the aid of coagulating agent. One of the major factors that determines the characteristics of the PRP is the substance that will be added into the preparations and provide clotting.

Platelet Rich Fibrin (PRF): Platelet Rich Fibrin (PRF) is defined as the autologous fibrin biomaterial rich in leukocyte and platelet. Unlike other platelet rich products, in this technique no anticoagulant, bovine origin thrombin, calcium chloride, or gelling agent are required. In this technique, blood is taken into the glass-coated plastic or glass tubes without delay and centrifuged at appropriate rpm. As a result of centrifuge, three layers occur through natural clotting in the tube, inducing by the silica content in the glass.

The layer of red blood cells accumulated at the bottom of the tube,
Acellular platelet-poor plasma accumulates on top of the tube,
The fibrin formed rich in platelets and leukocytes, that is, PRF clot occurs in the central part of the tube.

Leukocyte and platelet rich clot created through natural coagulation mechanism with centrifuging is obtained without any biochemical modifications of blood.

PRF Protocol:
The protocol used in the PRF application today:
Venous blood taken from the patient (~10 ml) is immediately placed inside a glass-coated plastic or glass tube containing no anticoagulant.
Tube is placed into the centrifuge set for 12 minutes 2700 rpm (speed) or 10 minutes 3000 rpm, and it is centrifuged.
After centrifugation, the layer of red blood cells accumulates at the bottom of the tube, acellular platelet-poor plasma on top of the tube, and fibrin, that is, PRF fibrin clot occurs in the central part of the tube.
PRF clot creates the fibrin matrix. A large number of blood taken platelets and leukocytes are collected in this fibrin matrix.
The released fibrin can be used in this manner by removing it with a tweezer from the tube or can be compressed into a membrane.

Platelet Rich Fibrin (PRF) and Platelet Rich Fibrin (PRF) membrane applications in medicine and dentistry:
Reinforcement of soft tissue healing,
In guided tissue regeneration with bone grafting and in directed bone regeneration applications,
In the closure of the sinus membrane perforation.

In addition, PRF can be used in the repair of acquired or generated osseous defects and in the primary or secondary bone loss which can be formed around the dental implant.

The disadvantages arising from the acquisition of Platelet Rich Fibrin from using a glass-coated plastic or glass tubes are as follows:

The exposure duration of PRF in tissues obtained from the glass and glass coated plastic tube is not effective enough for hard tissue healing.

It has been alleged that the silica particles in the content of glass that induce coagulation have harmful effects on tissues.

Platelet Rich Fibrin generated in the titanium tube (T-PRF): Titanium; is a corrosion resistant, biocompatible material and has a feature that osteointegrates to bone tissue. Because of this feature it is also used in dental implants. Moreover, titanium is a material suitable for producing platelet-rich fibrin and other blood products. As we defined in our previous invention (registered with TR201109999 number for patent application), the tubes with their blood contacting surfaces are made of pure titanium or titanium alloy are more successful in the platelet aggregation than the glass and glass-coated silicone tubes.

In addition, in order to obtain a better quality platelet-rich fibrin; increasing the surface area of a tube that contacts with blood gives positive results. Increasing the blood contacting surface of tube consisting of pure titanium or titanium alloy is performed with sandblasting, laser and the like. Thus, the quality and acquisition speed of the platelet-rich fibrin blood is raised by increasing the contact surface with pure titanium. As T-PRF has a tighter fibrin structure than glass PRF, its residence time in the tissue is much longer. It can be employed alone as a graft material in bone healing.

The formed fibrin must be removed from the tube carefully or else the mistakes that will be made will cause damage to fibrin. Since the stem cells are dense in the lower part of the fibrin, it is important to fix this part to the surface that is desired to be healed. During the fixation of fibrin to the soft tissue surfaces desired to improve, tearing and disintegration may occur. Fibrin fixation cannot be achieved in hard tissues owing to the lack of resistance. A desired result cannot be taken without fixed fibrin.

Calcium phosphates: It is a name given to calcium phosphates, orthophosphates, metaphosphates, or pyrophosphates, and especially to a family of minerals containing calcium ions with hydrogen ions or hydroxide.

Calcium is the most abundant mineral found in the body. It is the main constituent of bones and teeth. In addition, calcium plays an extremely important role in cessation of bleeding. Calcium is a coagulation factor stopping bleeding by allowing clot formation. In this case, calcium ions ($Ca^{2+}$) are involved as a cofactor.

99% of the calcium in the body exists in bone and teeth, and the remainder 1% is found in the blood and soft tissues. Calcium levels in the blood must be within a narrow range of concentrations for the realization of physiological functions. Inadequate calcium intake is important in terms of the risk of bone fractures or osteoporosis. Adequate calcium intake is a critical factor for a healthy skeletal system.

Because of the chemical similarity of calcium phosphate to bone and teeth, their biocompatibility and non-toxic characteristics to the body are known.

Hydroxyapatite and tricalcium phosphate are used most in the calcium phosphate compounds. It is important that these two calcium compounds occur in skeletal structure, similar crystallographic structure and chemical composition. Calcium phosphate compounds are used as graft materials, scaffold (the roof and the carrier) or used in order to increase implant osseointegration.

Calcium Phosphates
1—Monocalcium phosphate $Ca(H_2PO_4)_2$
2—Dicalcium phosphate $CaHPO_4$
3—Tricalcium phosphate $Ca_3(PO_4)_2$
4—Hydroxyapatite $Ca_5(PO_4)_3(OH)$
5—Apatite $Ca_{10}(PO_4)_6(OH, F, Cl, Br)_2$
6—Octacalcium phosphate $Ca_8H_2(PO_4)_6 \cdot 5H_2O$
7—Biphasic calcium phosphate Biphasic calcium phosphate is a good alternative to bone grafts for use around the implants and replaces living bone as it is resorbable.

Calcium-phosphate is the name given to calcium ion ($Ca^{2+}$) with ortho-phosphate ($PO_4^{3-}$), or pyro-phosphate ($P_2O_7^{4-}$), and sometimes to a mineral family consisting of hydrogen or hydroxide ions. Seventy percent of the bone consists of hydroxyapatite, a calcium phosphate mineral. Tooth enamel is largely calcium phosphate.

BRIEF DESCRIPTION OF THE INVENTION

Due to their chemical similarity of calcium phosphates, especially hydroxyapatite to bone and teeth, their biocompatibility is obvious. We have observed in our experiments that hydroxyapatite and other calcium phosphate compounds are the substances that form platelet aggregation. It is possible to form a better platelet aggregation and to obtain strong fibrin structure by placing these materials in the proper position compatible with the tube content. According to our experiment results, the existing of fibrin formed previously in the tube is also very important to achieve aggregation of fibrin to be formed newly. The invention is that the first occurred fibrin contributes to the maturation of new fibrin to be formed.

The invention is characterized by a fibrin compression container that is used to compress the fibrin structure, and an apparatus comprising at least one layer with a network structure to be used with tubes in order to obtain platelet rich fibrin. The mentioned network structure is attached to the fibrin carrier rod with clamps. The fibrin formed in the network of the apparatus is connected to the fibrin compression container with the help of fibrin carrier rod. The compression part in the fibrin compression container facilitates the separation of the fibrin carrier rod through pushing the network structure.

Fibrin will be formed stably around the layers of network structure that can be shaped and enriched with organic and inorganic materials that accelerate fibrin formation thanks to the kit placed into the tube. Substances that will increase the effect of the fibrin in wound healing may be added between the layers of the network structure. The resultant fibrin structure can be compressed and concentrated with the help of fibrin compression container and can be used easily. As the form of surface to be applied contains network structure and the network with layers can be reshaped, the fixation to the surface will be quite easy and stable. More than one fibrin can also be compressed in layers, and agents that can accelerate wound healing and guide can be added between the layers.

MEANINGS OF THE FIGURES

Figure 2:
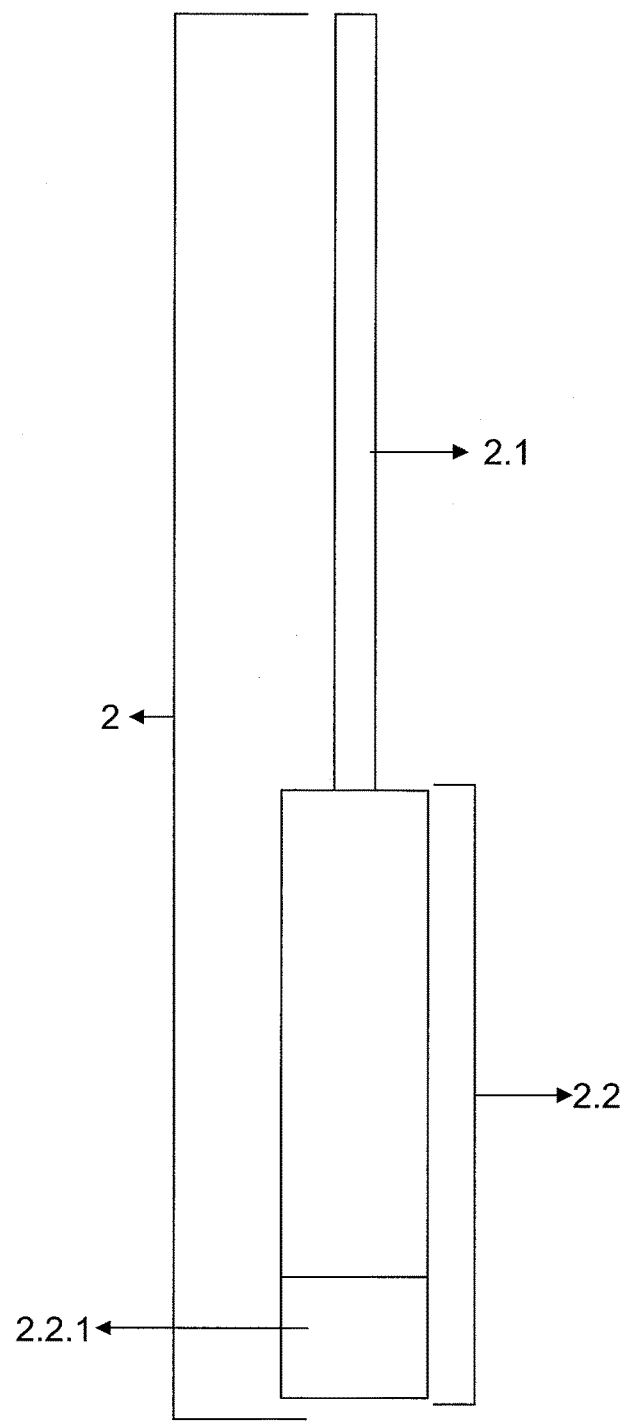
Figure 3:
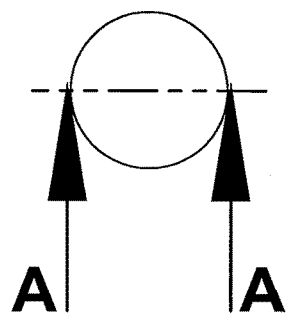
Figure 4:
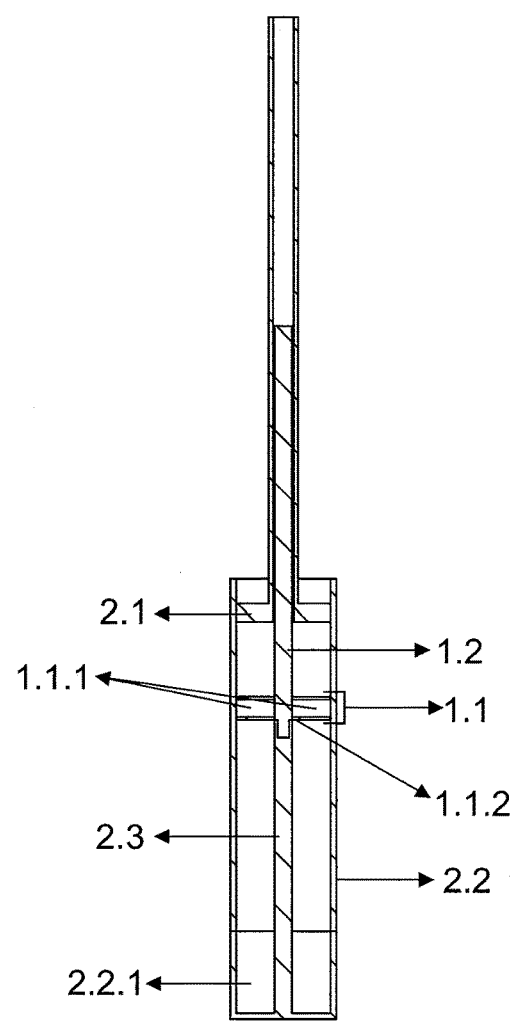
Figure 5:
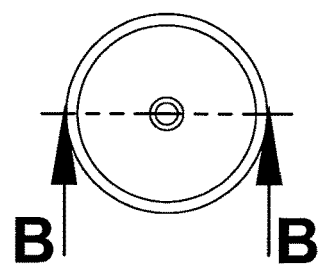
Figure 6:
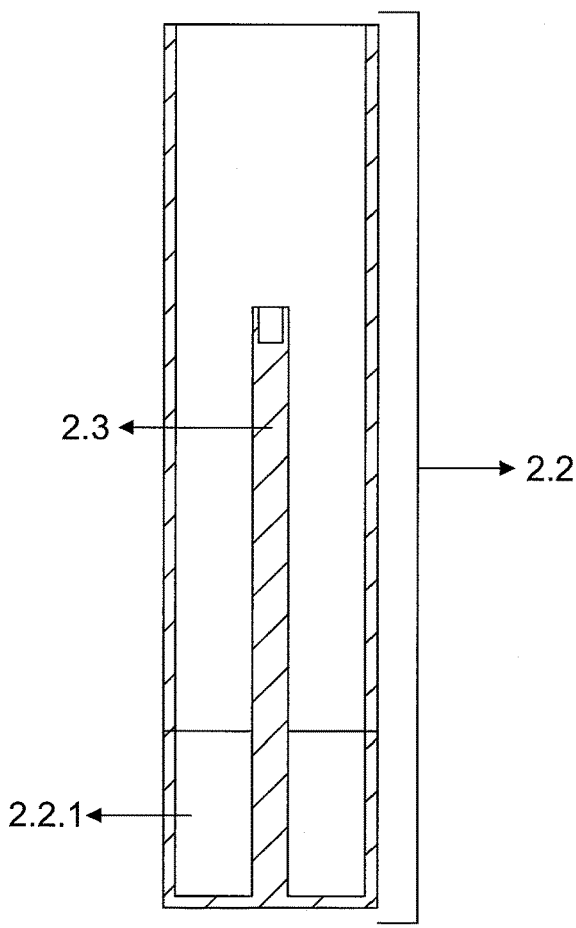
Figure 7:
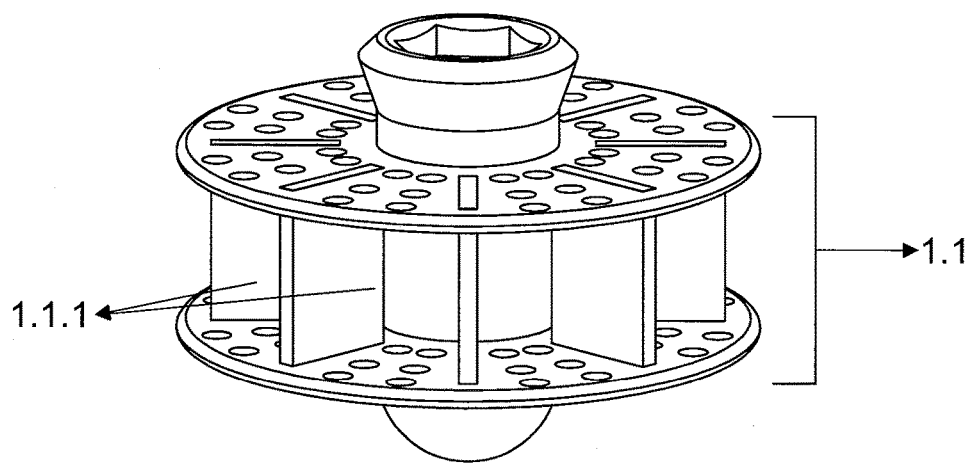

FIG. 1. Sectional View of the Fibrin Formation Apparatus
FIG. 2. Fibrin Compression Apparatus Mounted View
FIG. 3. Bottom View of Fibrin Compression Apparatus FIG. 4. Sectional View of Fibrin Compression Apparatus
FIG. 5. Top View of Fibrin Compression Container
FIG. 6. Sectional View of Fibrin Compression Container
FIG. 7. The View of Implant Placed into the Apparatus in Network Structure Equivalents of the specified part numbers are given below.
1. Fibrin generation apparatus
    1.1. Apparatus in the Network Structure
        1.1.1. Layer
        1.1.2. Clamp
    1.2. Carrier Rod
2. Fibrin Compression Apparatus
    2.1. Piston
    2.2. Container
        2.2.1. Removable Lower Base
    2.3. Carrier Rod Centralizer

DETAILED DESCRIPTION OF THE INVENTION

Invention is composed of fibrin generation apparatus (1) and Fibrin Compression Apparatus (2). Fibrin generation apparatus (1) consists of a network structured apparatus (1.1) with at least one layer (1.1.1) and clamps (1.1.2), and a carrier rod (1.2). Fibrin compression apparatus (2) is characterized by a piston (2.1) and container (2.2) containing a removable lower base (2.2.1), and a carrier rod centralizer (2.3).

Through the fibrin generation apparatus (1) inserted into the tube, shapeable fibrin is formed on the network structured apparatus. There is a network structured apparatus (1.1) containing at least one layer (1.1.1) attached with the help of clamps (1.1.2) to the end of the carrier rod (1.2). Network structured apparatus (1.1) consists of at least one layer (1.1.1). Calcium phosphate compounds, autogenous or non-autogenous graft materials, bone morphogenic proteins, fibroblast growth factors, bioactive agents such as PDGF, stem cells, puliripotent cells and fibrin or collagen obtained from the patient himself that accelerate fibrin formation before or after centrifugation and provide 3D wound healing can be inserted between these layers. These layers (1.1.1) can be shaped according to the surface to apply the fibrin. Upon completion of the centrifugation, apparatus forming fibrin (1) removed from the tube is attached to the carrier rod centralizer (2.3) of the fibrin compression apparatus (2) with the help of a carrier rod (1.2). When the piston (2.1) fixed on the carrier rod (1.2) is pushed, it will compress the network structured apparatus (1.1) pushing towards the removable lower base (2.2.1) of the container (2.2). Thus, compressed fibrin will be collected on the removable bottom base (2.2.1) of the container (2.2). A thick fibrin in layers can be formed by repeating this process many times. By changing the form of the piston (2.1) and the removable lower base (2.2.1), the shape of the fibrin can also be changed at this stage. Calcium phosphate compounds, autogenous or non-autogenous graft materials, bone morphogenic proteins, fibroblast growth factors, bioactive agents such as PDGF, stem cells, puliripotent cells, fibrin or collagen obtained from a patient himself can be inserted between the fibrin layers. These agents added according to the intended use will make fibrin more advantageous. Even this structure can act as a matrix to create artificial organs. By removing the removable bottom base (2.2.1) of the container (2.2), fibrin-based structure can be removed and used. Coating the fibrin-carrier rod (1.2) and the inside of the tube with calcium phosphate will accelerate the fibrin formation.

By inserting stem cells, autogenous and bioactive grafts into the center (1.1.1) of network structured apparatus (1.1), three dimentional healing will be possible providing improvement from fibrin towards tissues beside healing from the known wound towards fibrin.

Considering that the mechanism of coagulation and healing are different in the soft tissues and bone tissues, the fibrin to be used in these areas should be prepared according to different needs. Platelet-rich fibrin prepared nowadays is obtained by centrifuging the blood taken from the person in the glass or titanium tubes. The obtained platelet-rich fibrin is applied directly to the bone or soft tissues. This situation leads to less obtained gain. The healing in the healing model of the fibrins obtained through known technique occurs from tissue towards fibrin and when tissue absorbs fibrin in time. Stem cells, autologous grafts and bioactive grafts to be placed into the center of our invention with a layered structure can carry out three-dimensional model of healing.

This inventive kit is characterized by a network structured apparatus with at least one layer composed of biocompatible materials (calcium phosphate, titanium/titanium alloy, or calcium phosphate-coated titanium wire, bioceramics, resorbable polymers, etc.). The network structured apparatus can completely be resorbed or can remain biocompatible in tissue. The effect obtained from the treatment can be increased by putting auxiliary agents that help wound healing, accelerate and enhance organic and inorganic fibrin formation suitable to the tissue to be applied fibrin between the layers of fibrin formed in layers in the compression apparatus. These agents can be calcium phosphate compounds, autogenous or non-autogenous graft materials, bone morphogenetic proteins, growth factors, bioactive agents such as PDGF, stem cells, puliripotent cells, fibrin or collagen obtained from the patient himself. In addition, with the stem cells and autogenous grafts suitable to the tissue to be placed in the center of layers, three dimentional healing can be achieved from tissue to fibrin and from fibrin center to tissue. This will speed up the healing process.

The result obtained from the treatment may be increased by putting auxiliary agents that help wound healing, promote the formation and quality of organic and inorganic fibrin suitable to the tissue to be applied. These agents are calcium phosphate compounds, autogenous or autologous without graft material, bone morphogenetic proteins, growth factors, bioactive agents, such as PDGF, stem cells, puliripotent cells, fibrin or collagen obtained from the patient himself. In addition, the center layer of tissue with stem cells or autologous graft tissue to be appropriate fibrin may be provided with accurate three-dimensional tissue recovery from fibrin center. This will speed up the healing process.

The fixation of platelet-rich fibrin in both soft tissue and bone tissue is rather a huge problem. Delicate and flabby structured platelet-rich fibrin can be very quickly deformed. In addition, it is highly difficult for a physician to shape it according to the form of the area to be applied. Because it is important to place the bottom part where stem cells are dense to the recovery surface during the fibrin formation and to remain there stable for the treatment efficiency.

Network structured apparatus makes it possible for the physician to form it suitable to the area to be applied. Thus, the fibrin form that will occur on the network structured apparatus can be adjusted to the recovery surface form accordingly. In addition, during the fibrin fixation to this surface, suturing from network structure to the soft tissue or screwing it onto the hard (bone) tissue will cease to be a problem. Thus, the recovery surface will be merged with the surface heavily densed with fibrin stem cells in a stable manner.

The fact that network structured apparatus can be installed and uninstalled with the aid of a bead seat to the carrier rod is the convenience for the physician during use. Fibrin can be removed from the tube very easily and can be moved into the fibrin compression apparatus. He can use the platelet-rich fibrin right away taking it easily and without the risk of distortion the form from the tube or he can use it compressing in the compression container. The body of the network structure comprises pores the thorough which all elements of the blood can pass during centrifugation. It is not certainly in the selectively permeable membrane structure. It has the space that allows all blood elements to pass, and does not prevent the formation of fibrin. Its function is to form a frame and to hold the fibrin inside that will create the materials to be added. The network between the layers of the network structured apparatus will be woven in a suitable form and size of the material to be placed into the network layer between the layers of the network structured apparatus. More than one network structured apparatus can be connected to each other or the fibrin formed can provide connection as well. The network structured apparatus can be constructed in accordance with the geometric structure of the tube the body of which it is located in.

The implants can be coated with PRF stably by placing the implants to be coated with PRF between the layers (1.1.1) of network structured apparatus (1.1).

Network structured apparatus wraps around the implant without contacting the implant and fixing on the implant, and it allows the formed fibrin to remain stably around the implant. Network structured apparatus is fixed to the implant from different parts. Still, materials to promote and guide healing are added between the network structured apparatus and implant. Network structured apparatus will provide the required primary stability while the implant is placed into the body by receiving support from the walls of the space where the implant will be located, and immobilizing the implant. Thus, the fibrin thickness between the implant and the network structure is maintained, and the effect of fibrin on the healing and osseointegration is increased. Therefore, the adaptation and improvement process of the implant to the area where it is located will be positively affected. In parallel to the development of centrifugal technology, the size of the implants will cease to be a problem.

The invention claimed is:

1. A three-dimensional healing kit comprising a fibrin generation apparatus containing a network structured apparatus and a carrier rod and a fibrin compression apparatus; wherein the fibrin generation apparatus is separated from the fibrin compression apparatus, and the fibrin generation apparatus is inserted into a tube to perfume a centrifugation to separate a fibrin on the network structured apparatus from blood;

the network structured apparatus comprises an agent for accelerating a platelet aggregation and formation of the fibrin; and wherein the fibrin contacts with the agent to form a platelet rich fibrin, and the agent is one or more selected from the group consisting of calcium phosphate compounds, titanium, collagen, bioceramics and resorbable polymers.

2. The three-dimensional healing kit of claim 1, wherein the fibrin compression apparatus comprises a piston, a container and a carrier rod centralizer; wherein the fibrin generation apparatus is attached to the carrier rod centralizer.

3. The three-dimensional healing kit of claim 1, wherein the network structured apparatus comprises at least one layer.

4. The three-dimensional healing kit of claim 1, wherein the network structured apparatus comprises pores; and wherein elements of the blood that pass through the pores during the centrifugation remain in the tube.

5. The three-dimensional healing kit of claim 1, wherein the network structured apparatus has a structure that is shaped in accordance with a surface where the network structured apparatus is applied.

6. The three-dimensional healing kit of claim 2, wherein the container comprises a removable bottom base.

7. The three-dimensional healing kit of claim 3, wherein the network structured apparatus comprises at least two layers; wherein an auxiliary wound healing agent is inserted between two of the layers; and wherein the auxiliary wound healing agent accelerates and enhances a formation of an organic and inorganic fibrin suitable to a tissue to be applied; and the auxiliary wound healing agent is one or more selected from the group consisting of implants, calcium phosphate compounds, autogenous or non-autogenous graft materials, bone morphogenic proteins, fibroblast growth factors, bioactive agents, PDGF, stem cells, pluripotent cells, fibrin and collagen obtained from a patient.

8. The three-dimensional healing kit of claim 3, wherein the at least one layer is in a suitable form and size of a material to be placed into pores of the network structured apparatus; wherein the material is one or more selected from the group consisting of calcium phosphate, titanium/titanium alloy, calcium phosphate-coated titanium wire, bioceramics, and resorbable polymers; and the material accelerates fibrin formation.

* * * * *